United States Patent
Denis et al.

(10) Patent No.: US 7,803,174 B2
(45) Date of Patent: Sep. 28, 2010

(54) DORSAL ADJUSTING MULTI-ROD CONNECTOR

(75) Inventors: Francis Denis, Minneapolis, MN (US); Timothy Garvey, Edina, MN (US); Joseph Perra, Shoreview, MN (US); Manuel Pinto, Minnetonka, MN (US); James Schwender, Edina, MN (US); Ensor Transfeldt, Edina, MN (US); Michael S. Veldman, Memphis, TN (US); William A. Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 285 days.

(21) Appl. No.: 11/266,991

(22) Filed: Nov. 4, 2005

(65) Prior Publication Data

US 2007/0123860 A1    May 31, 2007

(51) Int. Cl.
*A61B 17/70* (2006.01)
(52) U.S. Cl. ................................ 606/250; 606/278
(58) Field of Classification Search .............. 606/61, 606/70–73, 60, 246–279, 290, 324; 403/167, 403/169, 174, 175, 177, 186
See application file for complete search history.

(56) References Cited

U.S. PATENT DOCUMENTS

| | | | |
|---|---|---|---|
| 4,653,481 A | 3/1987 | Howland et al. | |
| 4,920,959 A | 5/1990 | Witzel | |
| 5,024,213 A | 6/1991 | Asher | |
| 5,030,220 A | 7/1991 | Howland et al. | |
| 5,176,680 A | 1/1993 | Vignaud et al. | |
| 5,330,473 A * | 7/1994 | Howland | 606/61 |
| 5,476,462 A * | 12/1995 | Allard et al. | 606/60 |
| 5,582,612 A | 12/1996 | Lin | |
| 5,613,968 A | 3/1997 | Lin | |
| 5,716,355 A | 2/1998 | Jackson et al. | |
| 5,810,817 A | 9/1998 | Roussouly | |
| 5,910,142 A | 6/1999 | Tatar | |
| 5,938,663 A * | 8/1999 | Petreto | 606/61 |
| 5,944,327 A * | 8/1999 | Kanaan | 279/51 |
| 6,267,765 B1 | 7/2001 | Taylor | |
| 6,413,258 B1 | 7/2002 | Bernhardt | |
| 6,565,564 B2 * | 5/2003 | Hoffman et al. | 606/59 |
| 6,565,569 B1 | 5/2003 | Assaker et al. | |
| 6,569,164 B1 | 5/2003 | Assaker et al. | |
| 6,585,737 B1 | 7/2003 | Baccelli et al. | |
| 6,610,062 B2 | 8/2003 | Bailey et al. | |
| 6,610,063 B2 * | 8/2003 | Kumar et al. | 606/61 |
| 6,626,906 B1 * | 9/2003 | Young | 606/61 |

(Continued)

FOREIGN PATENT DOCUMENTS

EP    0 737 448    10/1996

(Continued)

*Primary Examiner*—Eduardo C Robert
*Assistant Examiner*—Tara R Carter

(57) ABSTRACT

An orthopedic implant is disclosed having at least one passage for an elongated member that is compressible. In certain embodiments, multiple compressible elongated member passages may be provided, or an elongated member passage may be U-shaped and closable by a closure member. Split ring members may be provided in compressible passages and around elongated members. A bone anchor may be connected to the implant so that locking the anchor to the implant compresses one or more of the elongated member passages.

25 Claims, 22 Drawing Sheets

U.S. PATENT DOCUMENTS

| | | |
|---|---|---|
| 6,749,612 B1 | 6/2004 | Conchy |
| 7,029,474 B2 * | 4/2006 | Richelsoph et al. ......... 606/252 |
| 7,261,715 B2 * | 8/2007 | Rezach et al. ................. 606/60 |
| 2002/0193795 A1 | 12/2002 | Gertzbein |
| 2004/0039388 A1 * | 2/2004 | Biedermann et al. ......... 606/71 |

FOREIGN PATENT DOCUMENTS

| | | |
|---|---|---|
| WO | WO 02/36026 | 10/1996 |
| WO | WO 03/026520 | 4/2003 |

* cited by examiner

DORSAL ADJUSTING MULTI-ROD CONNECTOR

The present disclosure generally relates to adjustable connector apparatus used for connection of tissue and/or implants with spinal rods. The apparatus can be useful for correction of spinal injuries or deformities.

In the realm of orthopedic surgery, it is well known to use implants to fix the position of bones. In this way, the healing of a broken bone can be promoted, and malformations or other injuries can be corrected. For example, in the field of spinal surgery, it is well known to place such implants into vertebrae for a number of reasons, including (a) correcting an abnormal curvature of the spine, including a scoliotic curvature, (b) to maintain appropriate spacing and provide support to broken or otherwise injured vertebrae, and (c) perform other therapies on the spinal column.

Typical implant and connection systems include several pieces, which commonly are useful and may be associated with only specific other pieces. Bone screws, hooks, and clamps are well known as fixation devices, which are connected or adjoined to a particular bone as a connection between the bone and the connection system which can include a support and/or stabilizing member such as a spinal rod. In such a system, a series of two or more screws may be inserted into two or more vertebrae to be instrumented. One or more rods or other elongated members are then placed within or coupled to the screws, or are placed within connecting device(s) that link the rod(s) and screw(s), and the connections are tightened. In this way, a rigid supporting structure is fixed to the vertebrae, with the rod providing the support that promotes correction or healing of the vertebral malformation or injury by keeping the vertebrae in a particular position.

DESCRIPTION OF THE ILLUSTRATED EMBODIMENTS

Figure 1:
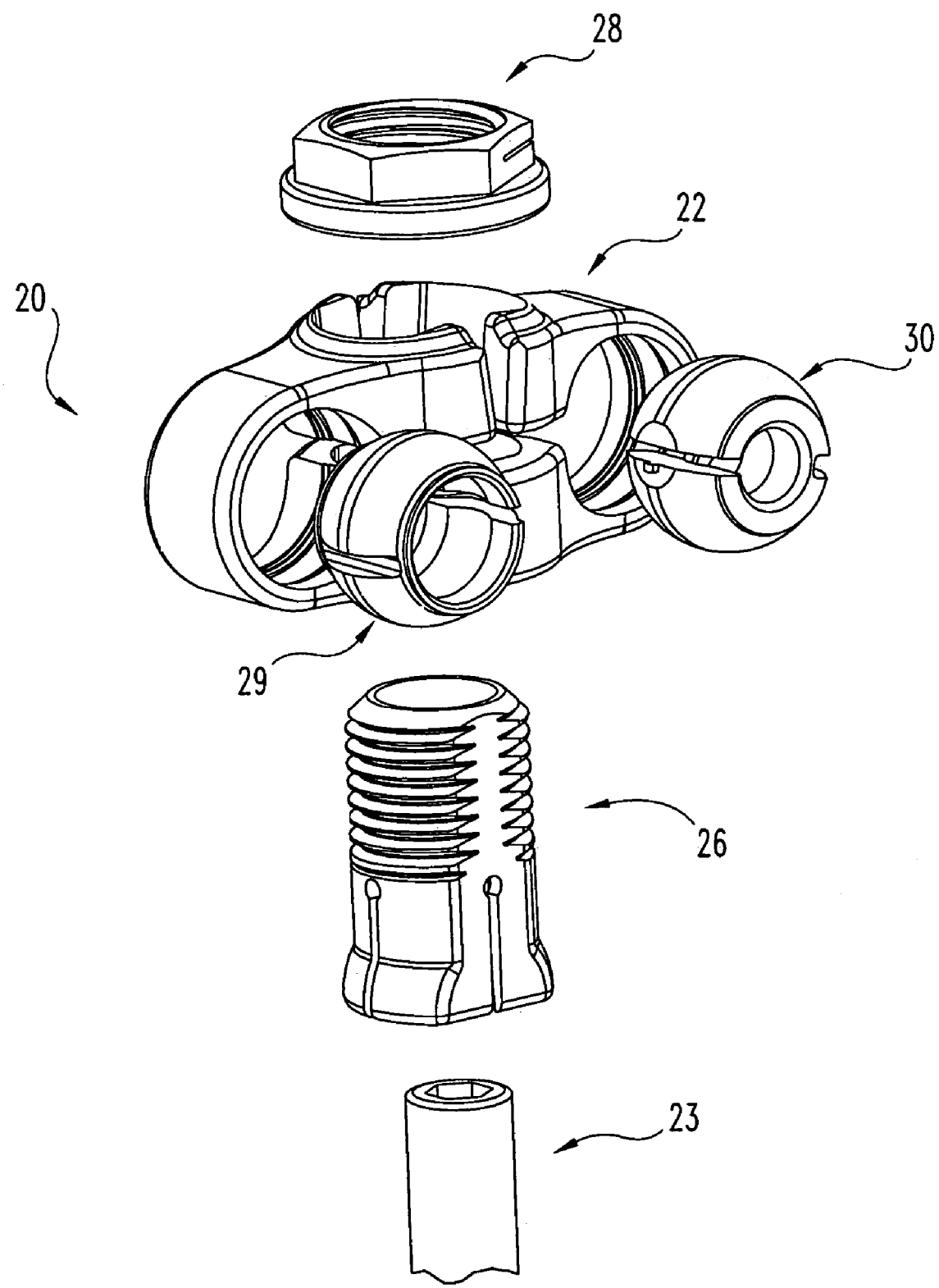
FIG. 1 is an exploded view in perspective a connecting assembly according to one disclosed embodiment.
Figure 2:
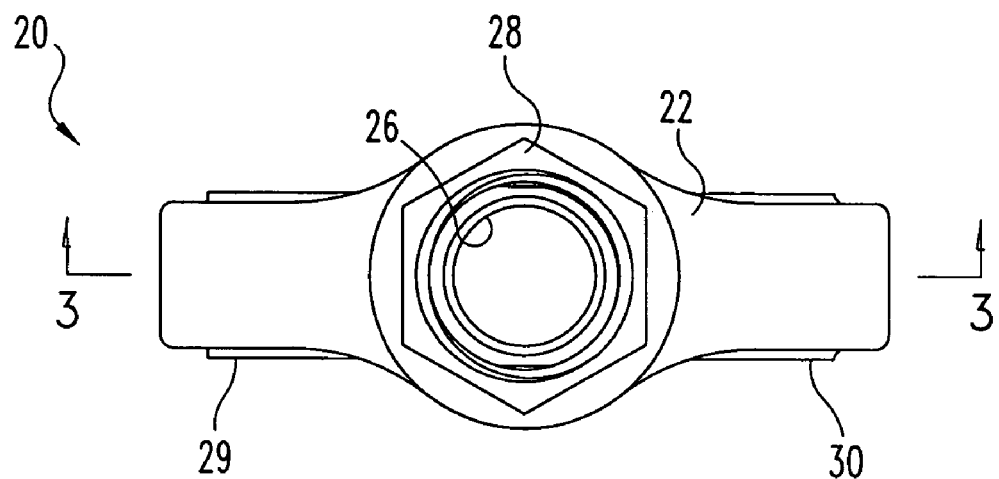
FIG. 2 is a top plan (non-exploded) view of the embodiment shown in FIG. 1.
Figure 3:
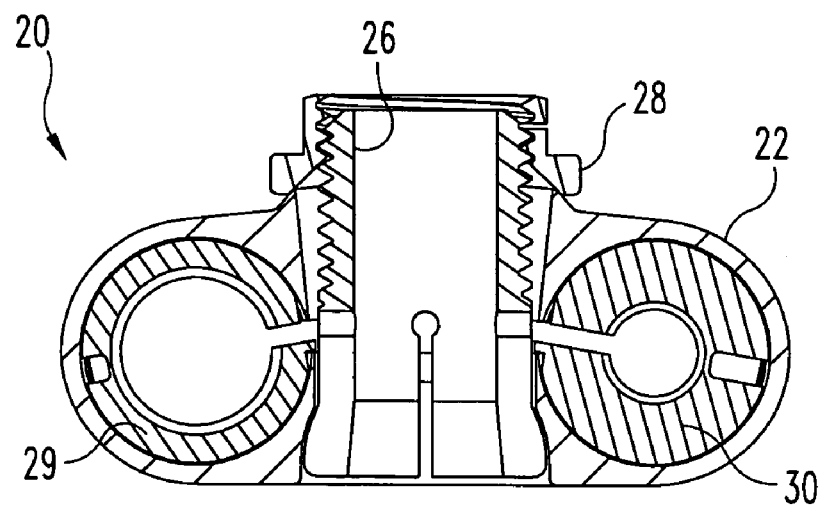
FIG. 3 is a cross-sectional view of the embodiment shown in FIGS. 1 and 2, taken along the lines 3-3 in FIG. 2 and viewed in the direction of the arrows.
Figure 4:
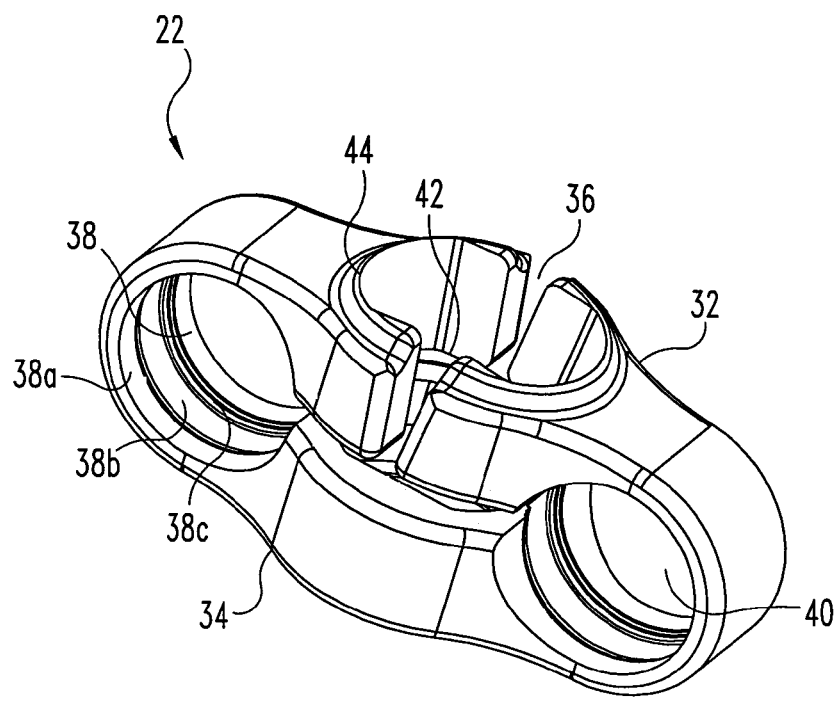
FIG. 4 is a perspective view of an embodiment of a body shown in FIG. 1.
Figure 5:
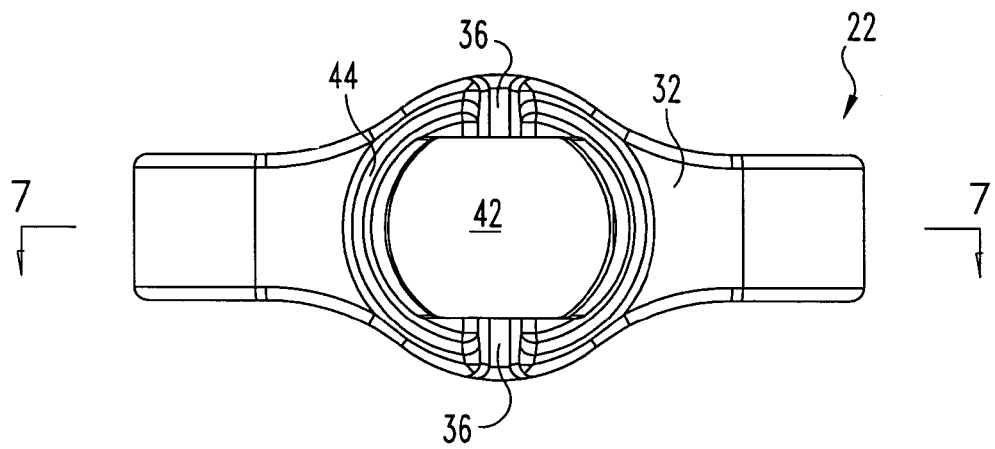
FIG. 5 is a top plan view of a body according to the embodiment shown in FIG. 4.
Figure 6:
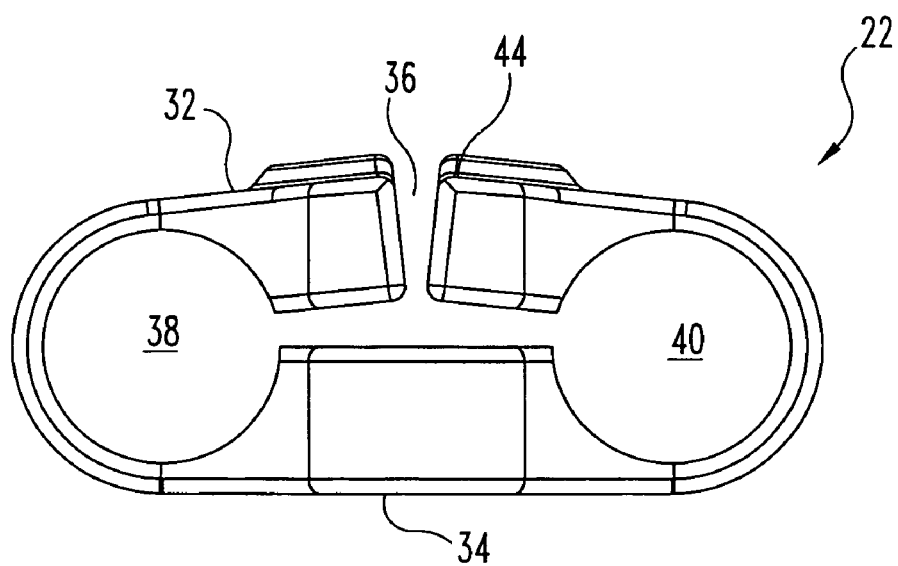
FIG. 6 is a side plan view of a body according to the embodiment shown in FIG. 4.
Figure 7:
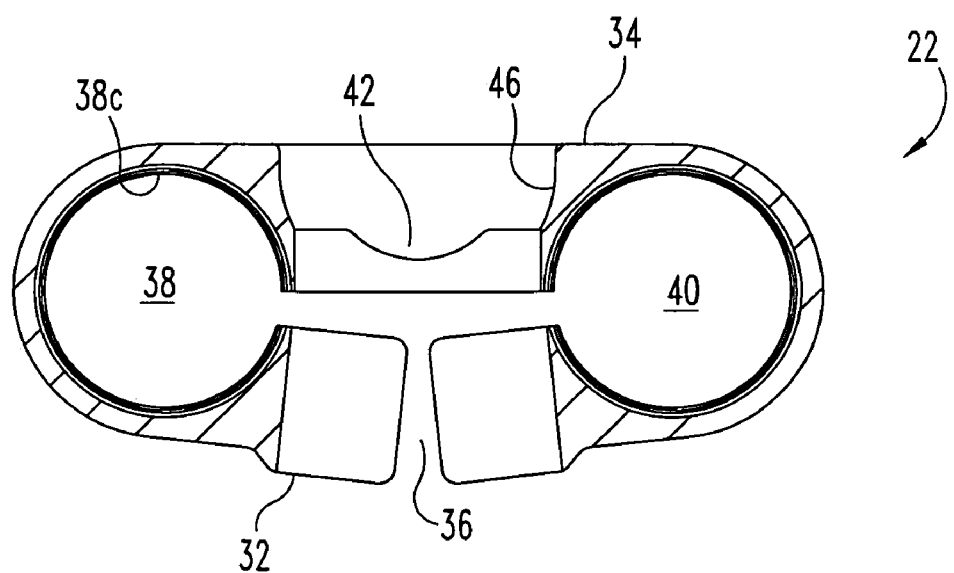
FIG. 7 is a cross-sectional view of a body according to the embodiment shown in FIG. 4, taken along the lines 7-7 in FIG. 5 and viewed in the direction of the arrows.
Figure 8:
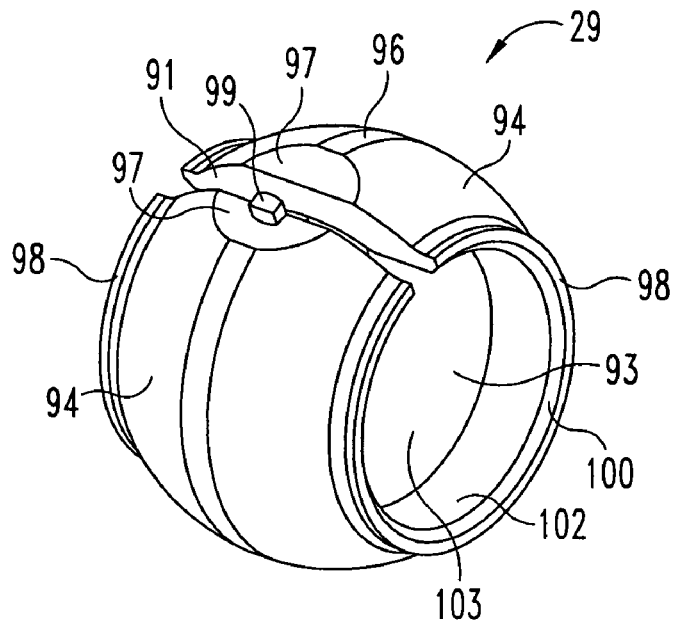
FIG. 8 is a perspective view of an embodiment of a split ring member shown in FIG. 1.
Figure 9:
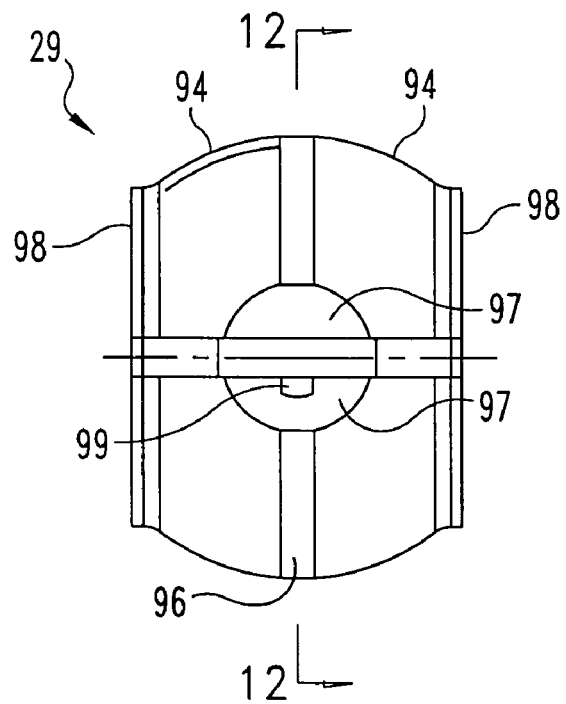
FIG. 9 is a side plan view of the embodiment shown in FIG. 8.
Figure 10:
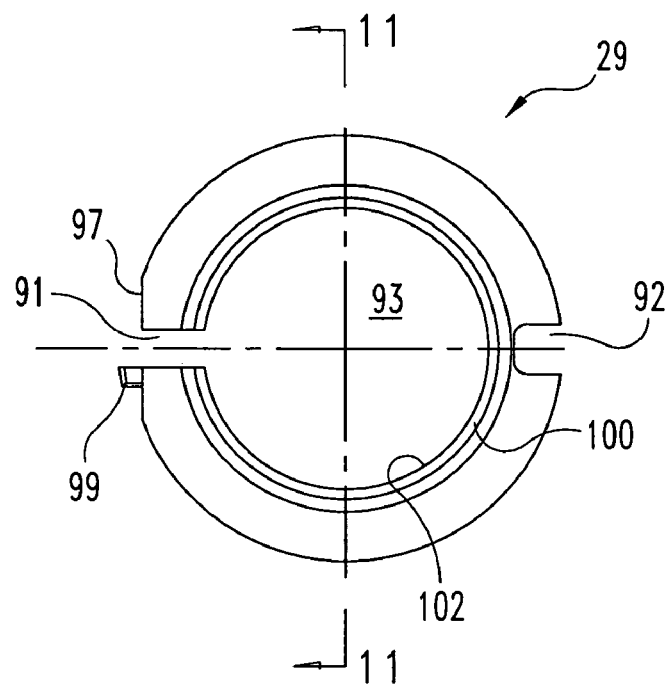
FIG. 10 is a side plan view of the embodiment shown in FIG. 8, rotated 90 degrees from the view shown in FIG. 9.
Figure 11:
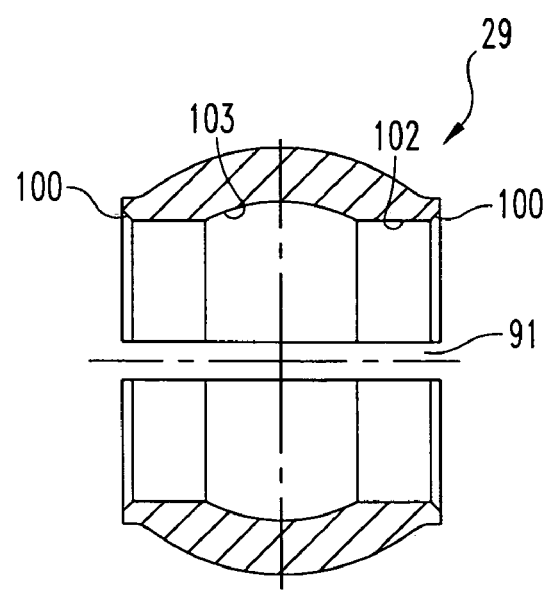
FIG. 11 is a cross-sectional view of the embodiment shown in FIG. 10, taken along the lines 11-11 in FIG. 10 and viewed in the direction of the arrows.
Figure 12:
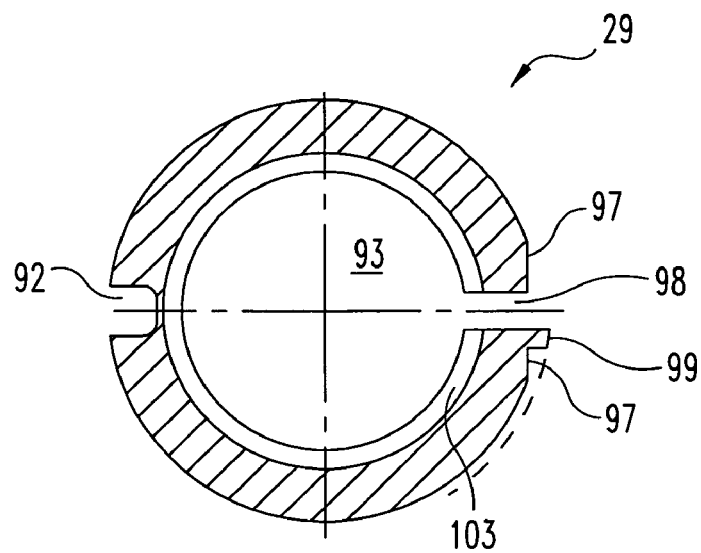
FIG. 12 is a cross-sectional view of the embodiment shown in FIG. 9, taken along the lines 12-12 in FIG. 9 and viewed in the direction of the arrows.
Figure 13:
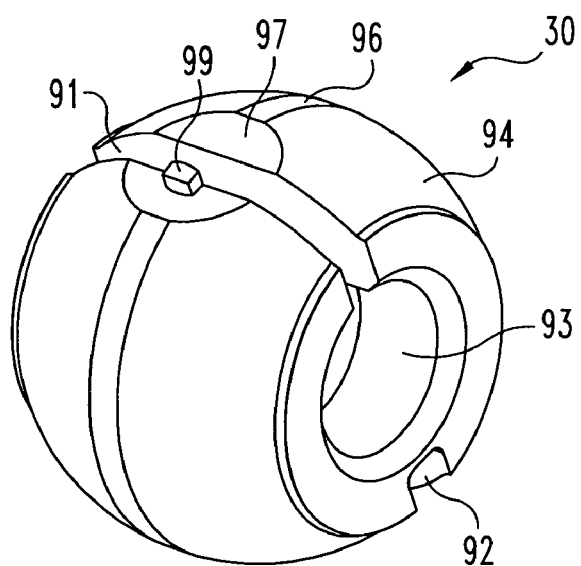
FIG. 13 is a perspective view of an embodiment of a split ring member shown in FIG. 1.
Figure 14:
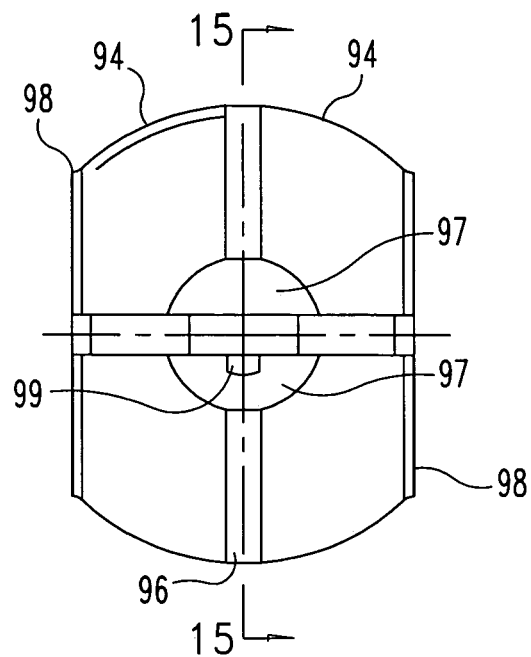
FIG. 14 is a side plan view of the embodiment shown in FIG. 13.
Figure 15:
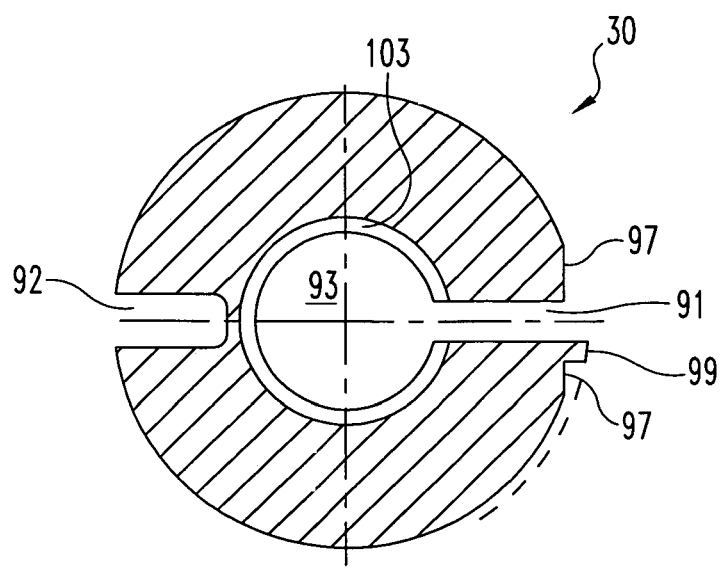
FIG. 15 is a cross-sectional view of the embodiment shown in FIG. 14, taken along the lines 15-15 in FIG. 14 and viewed in the direction of the arrows.
Figure 16:
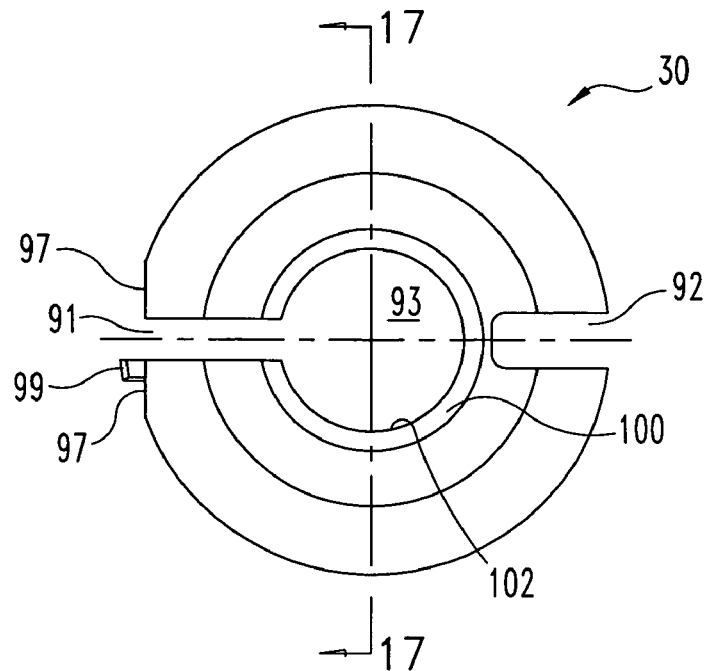
FIG. 16 is a side plan view of the embodiment shown in FIG. 14, rotated 90 degrees from the view shown in FIG. 14.
Figure 17:
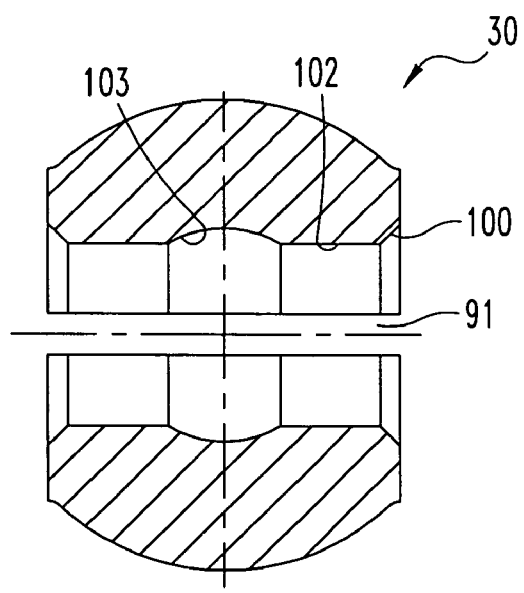
FIG. 17 is a cross-sectional view of the embodiment shown in FIG. 16, taken along the lines 17-17 in FIG. 16 and viewed in the direction of the arrows.
Figure 18:
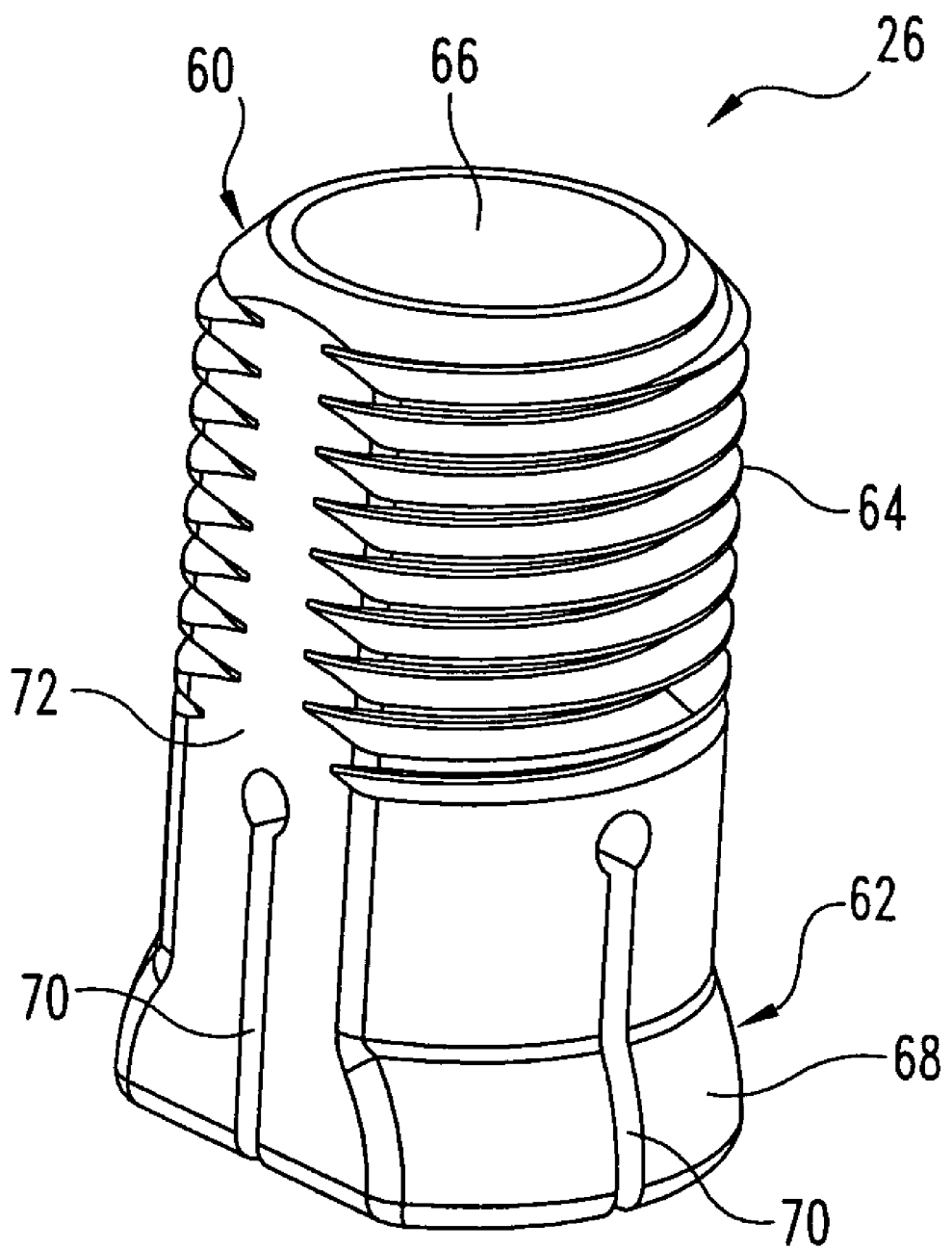
FIG. 18 is a perspective view of an embodiment of a collet member shown in FIG. 1.
Figure 19:
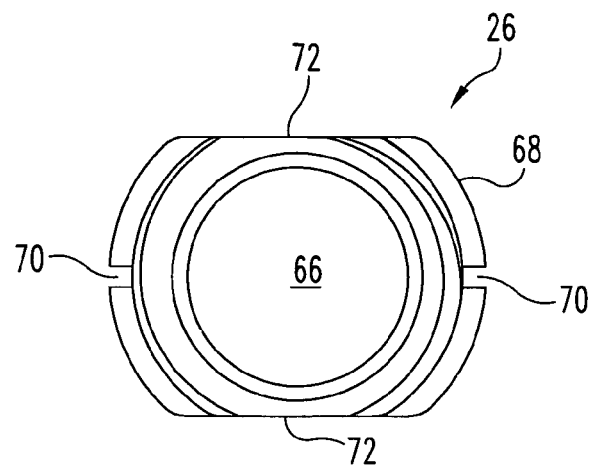
FIG. 19 is a top plan view of the embodiment shown in FIG. 18.
Figure 20:
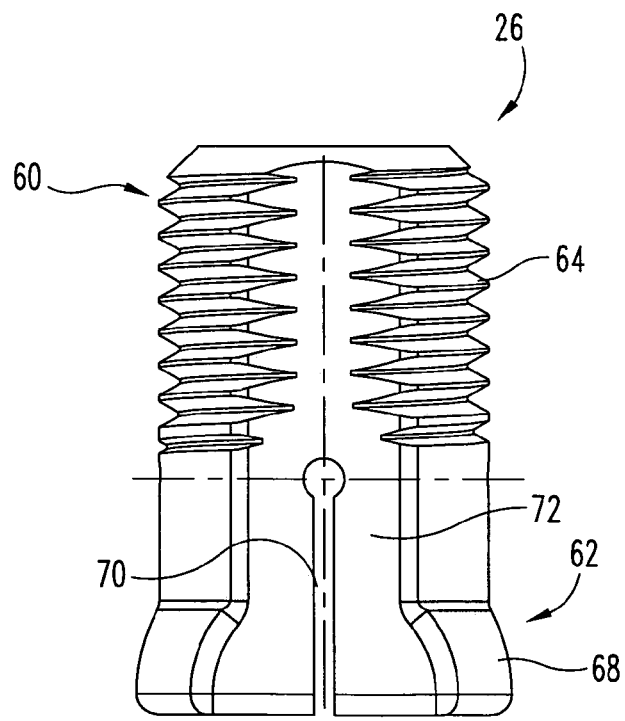
FIG. 20 is a side elevational view of the embodiment shown in FIG. 18.
Figure 21:
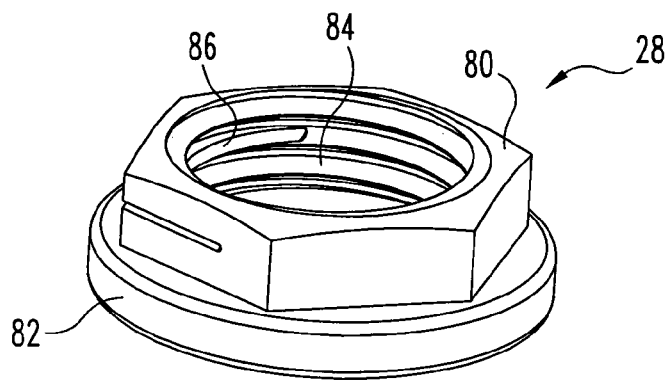
FIG. 21 is a perspective view of an embodiment of a nut shown in FIG. 1.
Figure 22:
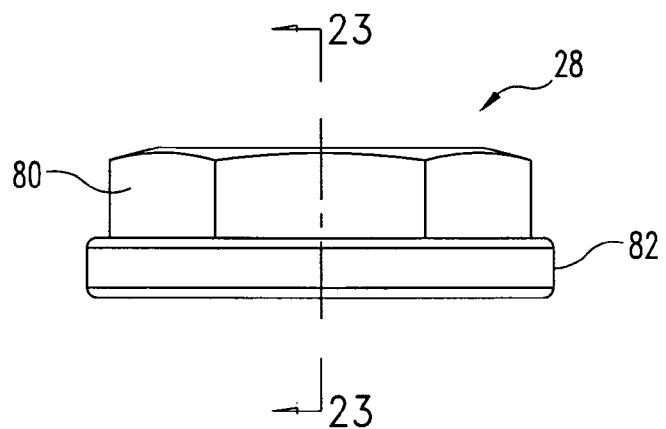
FIG. 22 is a side elevational view of the embodiment shown in FIG. 21.
Figure 23:
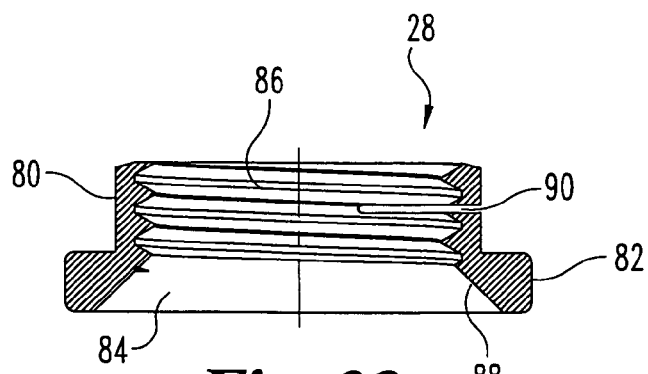
FIG. 23 is a cross-sectional view of the embodiment shown in FIG. 22, taken along the lines 23-23 in FIG. 22 and viewed in the direction of the arrows.
Figure 24:
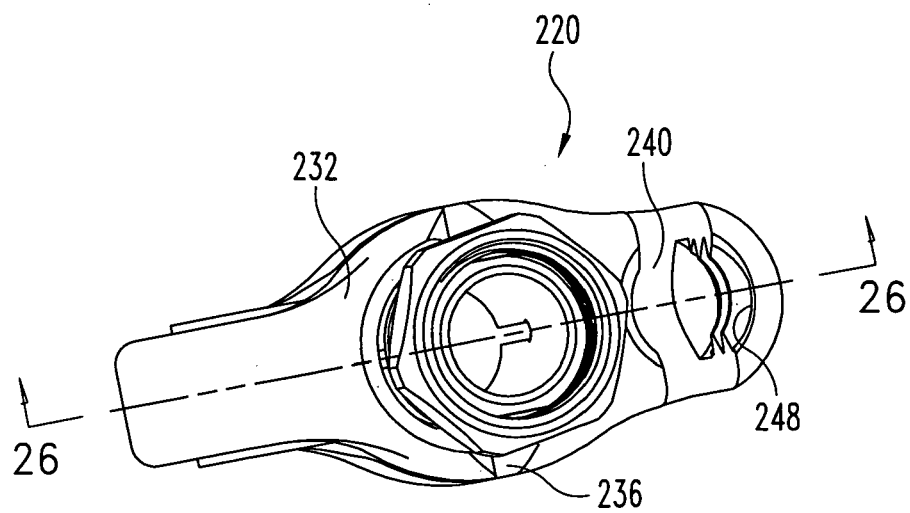
FIG. 24 is a perspective view of a connecting assembly according to one disclosed embodiment.
Figure 25:
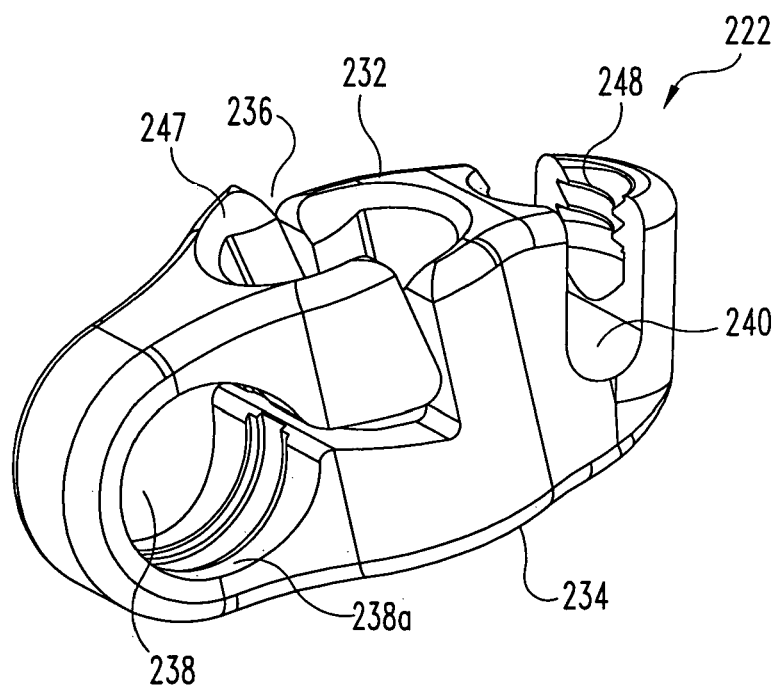
FIG. 25 is a perspective view of the embodiment of FIG. 24, rotated about 90 degrees from the view in FIG. 24.
Figure 26:
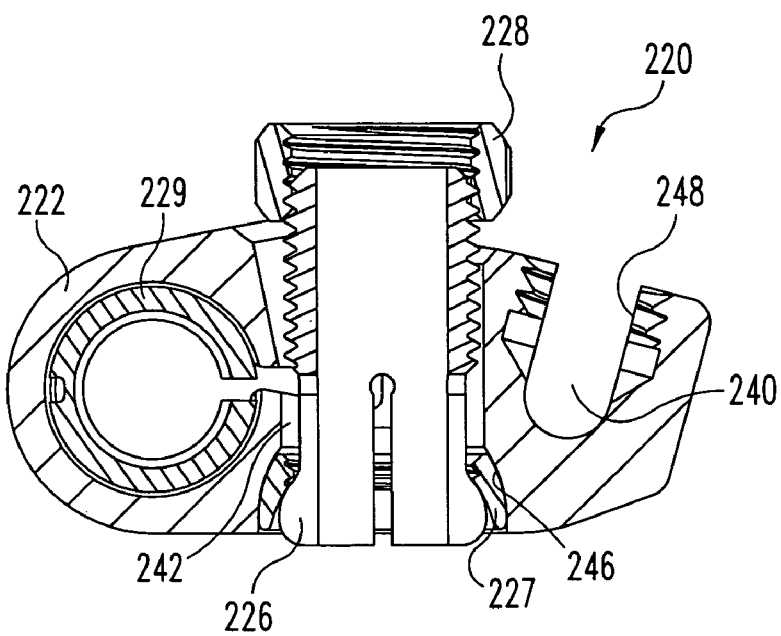
FIG. 26 is a cross-sectional view of the embodiment shown in FIG. 24, taken along the lines 26-26 in FIG. 24 and viewed in the direction of the arrows.

For the purpose of promoting an understanding of the principles of this subject matter, reference will now be made to the embodiments illustrated in the drawings and specific language will be used to describe the same. It will nevertheless be understood that no limitation of the scope of the claims is thereby intended, such alterations and further modifications in the illustrated device, and such further applications of such principles as illustrated therein, being contemplated as would normally occur to one skilled in the art to which this subject matter relates.

Referring to the drawings, there is shown an embodiment of an assembly 20 including a connecting body 22. Connecting body 22 is operable to connect an implant 23, such as a Schanz-type screw with a threaded anchoring portion, with one or more elongated members (not shown), which may be spinal rods, pins or similar structures. Implant 23 is inserted into or otherwise connected to a vertebra, and elongated members, in embodiments in which two or more are used, are utilized to maintain vertebrae in a desired position. It should be appreciated that the implant utilized in conjunction with body 22 can be any appropriate bone anchor or bone-engaging mechanism. Additionally, elongated members that may be connected to body 22 can be bars, connectors, or other orthopedic constructs of a variety of lengths. The embodiment of assembly 20 shown in FIG. 1 further includes a collet 26 to receive implant 23, nut 28, and split ring members 29 and 30.

One illustrated embodiment of body 22 has an upper portion or surface 32 and a lower portion or surface 34. Upper surface 32 is bifurcated in one illustrated embodiment by a slot 36 that may be substantially perpendicular to surface 32, or may be wedge-shaped or otherwise configured. Two passages 38 and 40 extend through body 22 and are between surfaces 32 and 34, and may be substantially parallel to each other. In a particular embodiment, passages 38 and/or 40 are substantially cylindrical throughout. In other embodiments, passages 38 and/or 40 may have a tapered or curved surface toward the surface of body 30 and a cylindrical surface in the interior of body 30, so that the cylindrical surface has a smaller internal diameter than the part of the passage adjacent the surface of body 30. Passages 38 and 40 may be substantially identical in size, or one passage may be somewhat larger than the other. Body 22 further defines a hole 42 extending therethrough and configured for receipt of anchor 23, as will be discussed further below. Hole 42 may be substantially perpendicular to passages 38 and 40. A lip or ridge 44, which may be substantially conical, curved or otherwise configured, may be formed on upper surface 32 to extend around at least a portion of hole 42. A concavely curved portion 46 is adjacent bottom surface 34. As alternatives, hole 42 may include a tapered, cylindrical or curved bowl portion adjacent top surface 32, and portion 46 may be tapered, cylindrical, or otherwise curved.

Passages 38 and 40 may have internal surfaces of one or more configurations that allow placement and locking of split ring members 29, 30 and/or rods or other elongated members in them. For example, in the illustrated embodiment passage 38 includes a tapered opening 38a on each side, to facilitate placement of a ring member in passage 38. Inside tapered opening 38a is a concave section 38b that may be approximately the same curvature as a portion of a split ring, and innermost is a section 38c that may be cylindrical, or may include edges or a stepped area. Passage 40 may be configured substantially the same as passage 38, or the passages may be configured differently from each other. In this embodiment, both passages 38 and 40 are compressible, as will be discussed further below.

In one illustrated embodiment, collet 26 includes a proximal end 60 and a distal end 62. A threaded portion 64 extends along at least a portion of proximal end 60. An aperture 66 extends through collet 26. Collet 26 further includes a convex section 68 adjacent distal end 62, the function of which will be explained in greater detail below. Additionally, collet 26 includes one or more slots 70. In one embodiment, there are four slots 70 equally positioned about a circumference of collet 26 and which are generally parallel to aperture 66. Collet 26 includes one or more flat sections 72. In one embodiment, collet 26 includes two flat sections 72 positioned substantially diametrically opposite each other along the outside of collet 26 and along substantially the entire length of collet 26. Flats 72 could be placed over only a portion of collet 26, e.g. on proximal end 60 or threaded portion 64. Collet 26 is generally cylindrically shaped, except for flat sections 72 (if any). The outer cross-sectional dimension of collet 26 at convex section 68 is larger than an outer cross-sectional dimension of collet 26 at other points in the illustrated embodiment. Proximal portion 60 of collet 26 is sized and shaped so as to fit and move easily within hole 42. However, collet 26 can be configured or shaped differently in other embodiments.

Figure 42:
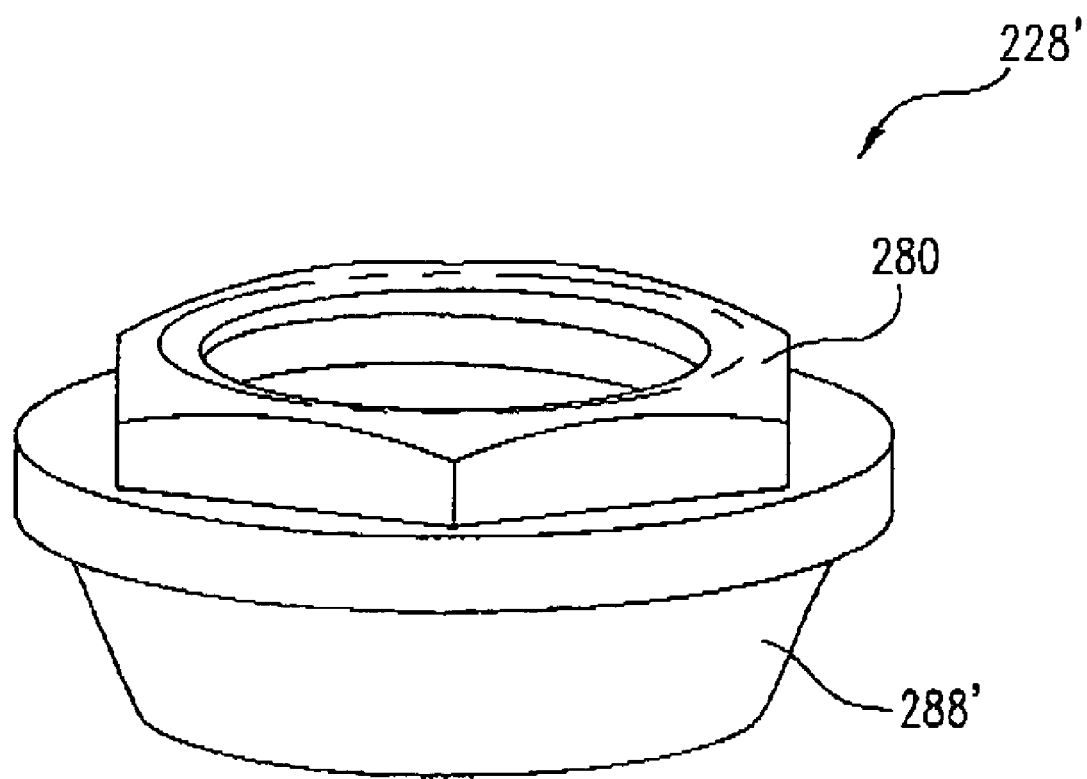
FIG. 42 is a perspective view of another embodiment of a nut.

Nut 28, in one embodiment, has a six-sided upper portion 80 and a round lower portion 82. A threaded hole 84 extends through nut 28, and has a threaded upper portion 86 and a tapered lower portion 88. A slit 90 may be provided through upper portion 80 and threaded portion 86 so as to help lock nut 28. Threaded portion 86 is configured to be threaded on threaded portion 64 of collet 26. In other embodiments, nut 28 can be of other shapes or configurations. In an embodiment of body 22 having a tapered bowl surface 47 adjacent upper surface 32, nut 28 may have a lower portion similar to that shown in FIG. 42, to closely contact much or substantially all of surface 47. In embodiments of body 22 having another surface configuration adjacent hole 42, nut 28 may be provided with a lower surface that closely fits such surface configuration.

The illustrated embodiment of ring member 29 is generally annular, having a gap 91, notch 92 and through-hole 93 to allow expansion and/or contraction of ring member 29. The outside of ring member 29 has generally convex portions 94, which in a particular embodiment may be spherical, and a substantially cylindrical portion 96. Cylindrical portion 96 is shown as lying in a plane that includes the center of the sphere in which convex portions 94 lie. Along cylindrical portion 96 and adjacent gap 91 lie one or more flattened areas 97, that in a particular embodiment are at least approximately semi-circular. Extensions 98 extend outward from convex portions 94 and substantially surround hole 93. Ring member 29 may include a tab or projection 99 extending from the outer surface of ring member 29, and in a particular embodiment in which ring member 29 includes one or more flattened areas 97, tab 99 may extend from one (or more if there are multiple tabs 99) of such flattened area 97. Tab 99 may be sized and configured to extend outside of the particular passage (e.g. passages 38 or 40) in which ring member 29 sits, and limits the rotation of ring member 29 so that its gap 91 remains generally adjacent to the middle of body 22. The inside of ring member 29 is for accommodating a rod, pin or other elongated orthopedic member, and in the illustrated embodiment includes tapered outer surfaces 100, a substantially cylindrical surface 102, and a concave (e.g. part-spherical) inner surface 103. Ring member 29 has unstressed or natural outer diameter, i.e. a diameter measured when ring member 29 is under no contractive (gap-closing) or expansive (gap-opening) stress. Ring member 29 has an inner dimension measured diametrically between points on cylindrical portion 102 that, in one embodiment, is at least slightly larger than a diameter or similar dimension of a rod, pin or other elongated member.

An embodiment of ring member 30 is also shown, and includes essentially the same features as discussed above with respect to ring member 29. Accordingly, the same reference numbers are used with respect to ring member 30 for aspects that are essentially the same as aspects of ring member 30. It will be seen that through-hole 93 of ring member 30 is shown somewhat smaller than hole 93 of ring member 29, and thus accommodates a somewhat smaller elongated member. In other embodiments, the sizes of the holes through the ring members 29 and 30 can be substantially similar or identical. Further, ring member 30 may include a tab or projection 99 extending from the outer surface of ring member 30, and in a particular embodiment in which ring member 30 includes one or more flattened areas 97, tab 99 may extend from one (or more if there are multiple tabs 99) of such flattened area 97.

The assembly, operation and use of assembly 20 will now be described with reference to a surgical procedure involving a section of spine. Ring members 29 and 30 are inserted into passages 38 and 40 of body 22. In embodiments in which one or both of ring members 29 and 30 have an unstressed outer diameter larger than the inner dimension of the respective passage 38 or 40, such ring member(s) may be compressed to fit in the respective passage, and released so that such ring member(s) sit within the respective passage. Collet 26 is inserted into hole 42 of body 22 so that at least part of threaded portion 64 extends above body 22, and convex section 68 of collet 26 is adjacent curved portion 46 of body 22. Nut 28 may be loosely threaded onto collet 26. These assembly steps may be performed in any of a variety of orders. For example, collet 26 may be inserted before ring members 29, 30 are inserted. As another example, one or both ring members 29, 30 may be fitted onto elongated members as described below, and then the elongated members and ring members can be inserted into passages 38, 40. As yet a further example, collet 26 may first be placed over a positioned bone anchor as described below, and then the combination of collet 26 and the bone anchor may be inserted into hole 42 of body 22.

Bone anchor 23, such as a Schanz-type screw, hook or other apparatus having a shank portion, is inserted into or otherwise connected to a bone, such as a vertebra (not shown). Assuming body 22, collet 26, nut 28 and ring members 29, 30 have been already assembled together as described above, assembly 20 is moved to a position adjacent anchor 23 and collet 26 is slid over the shank of anchor 23. Assembly 20 is positioned along the shank of anchor 23 as the surgeon desires, and thus assembly 20 can be located at any height over the bone within a range determined by the length of shank 122 exposed over the bone. It will be understood that anchor 23 may be placed first through collet 26 and/or body 22, and then threaded into a bone, if the surgeon so desires.

Elongated members are inserted through ring members 29, 30. Through-holes 92 of ring members 29, 30 may thus be thought of as passages for the elongated members. In some embodiments, elongated members may be inserted through one or both of ring members 29, 30 prior to placing assembly 20 over anchor 23, and in other embodiments one or both elongated members may be inserted through assembly 20 after it is placed over anchor 23. Once placed within ring members 29, 30 and assembly 20, one or both of the elongated members can be pivoted with respect to body 22 to any of a variety of angles. In doing so, ring members 29, 30 are rotatable within their respective passages 38, 40. The pivoting of ring members 29, 30 and/or their respective elongated members 24, 25 may be limited by contact of extension(s) 98 (if present on a respective ring member) with a surface of body 22 adjacent the respective passage 38, 40, or of tab 99 (if present on a respective ring member) with a relatively internal surface of body 22. If ring members having different size through-holes 92 and elongated members of differing diameter or width are used, then generally the smaller elongated member should be placed through the ring member with the smaller through-hole, and the larger elongated member should be placed through the ring member with the larger through-hole.

When elongated members are positioned with respect to body 22 as the surgeon desires, and assembly 20 is at the desired position with respect to anchor 23, the surgeon may tighten nut 28. In this embodiment, tightening nut 28 around collet 26 draws collet 26 in hole 42 so that bottom surface 34 forces convex section 68 to contract around anchor 23 by virtue of slots 70. Such contraction of collet 26 around anchor 23 locks anchor 23 with respect to collet 26 and body 22 at the desired relative position. At the same time, nut 28 exerts a pushing force on upper portion 32 of body 22. Such pushing forces both sides of upper portion 32 down, essentially pivoting both sides of upper surface 32 around respective axes in or near the sides of body 22 adjacent passages 38 and 40, and compresses passages 38 and 40. Compressing the passages results in similar compression of ring members 29, 30 within them, locking ring members 29, 30 around their respective elongated members. In embodiments in which passages 38 and/or 40 have edges or stepped portions, such edges or steps may bite into, penetrate or otherwise interact with a respective ring member to enhance the connection between body 22 and ring member 29 and/or 30. Thus, tightening nut 28 locks assembly 20 with respect to both anchor 23 and the elongated members.

An alternative embodiment of an assembly 220 is also shown. It is quite similar to assembly 20, discussed above, in many structural and functional features, and is assembled and used similarly. It is to be understood that most or all of the parts described above may be used with assembly 220, and that parts described below may replace or be used with parts described above with respect to assembly 20.

Assembly 220, in the illustrated embodiment, includes a connecting body 222. Connecting body 222 is operable to connect an anchor (e.g. anchor 23 shown in FIG. 1, to which reference will be made below), such as a Schanz-type screw or other implant with a shank, with one or more elongated members (e.g. spinal rods, pins or other orthopedic device). Assembly 220 includes a collet 226 to receive implant 23, washer 227, nut 228, and split ring member 229.

Figure 27:
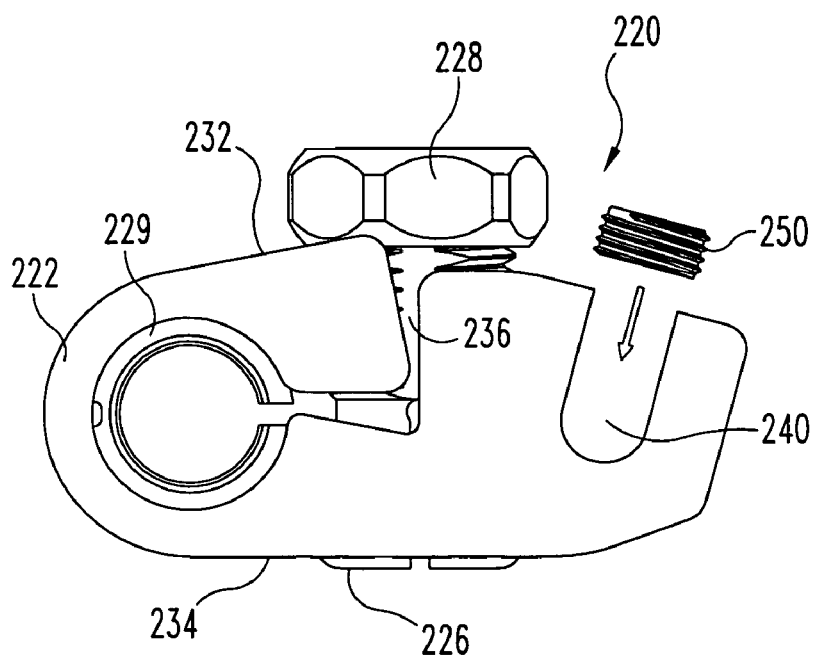
FIG. 27 is a side elevational view of the embodiment shown in FIG. 25.
Figure 28:
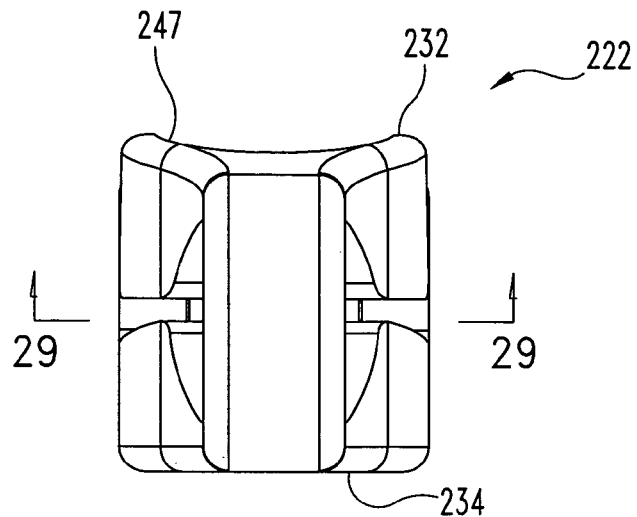
FIG. 28 is a side plan view of an embodiment of a body shown in FIG. 25.
Figure 29:
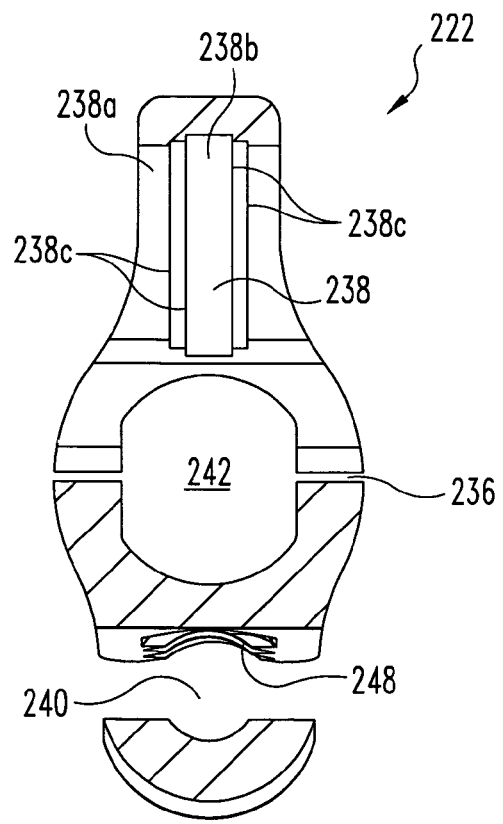
FIG. 29 is a cross-sectional view of the embodiment shown in FIG. 28, taken along the lines 29-29 in FIG. 28 and viewed in the direction of the arrows.
Figure 30:
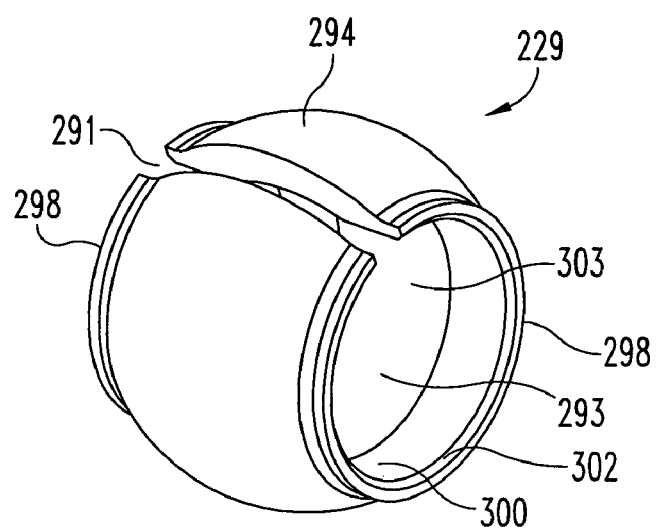
FIG. 30 is a perspective view of an embodiment of a split ring member shown in FIG. 25.
Figure 31:
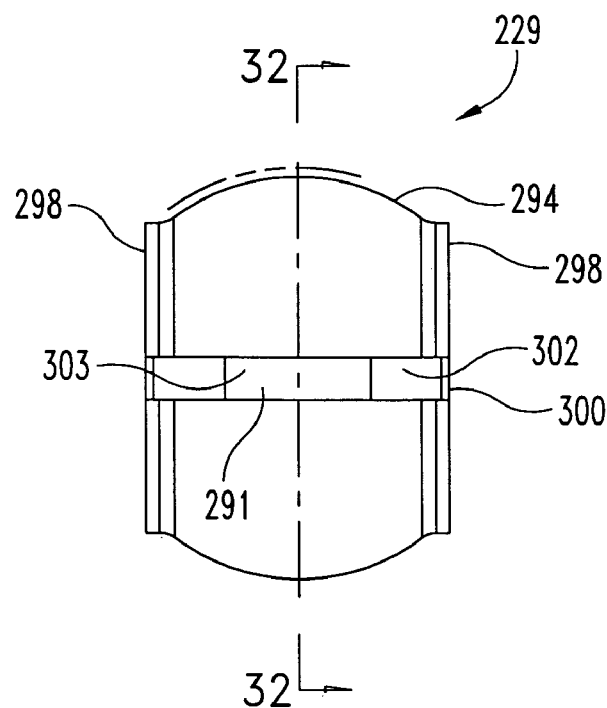
FIG. 31 is a side elevational view of the embodiment of a split ring member shown in FIG. 30.
Figure 32:
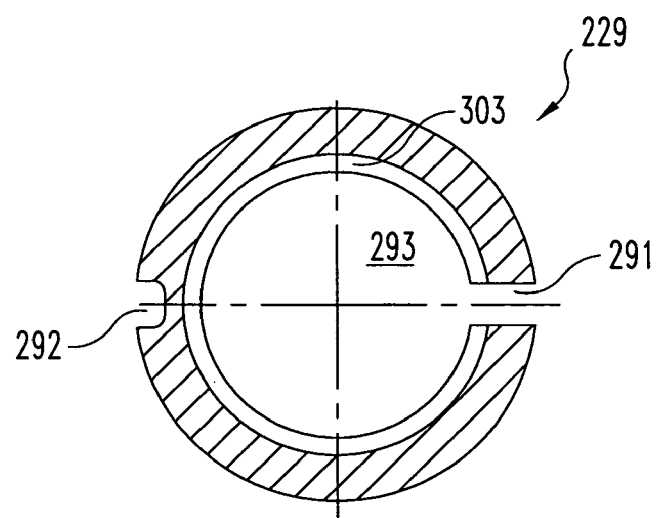
FIG. 32 is a cross-sectional view of the embodiment shown in FIG. 31, taken along the lines 32-32 in FIG. 31 and viewed in the direction of the arrows.
Figure 33:
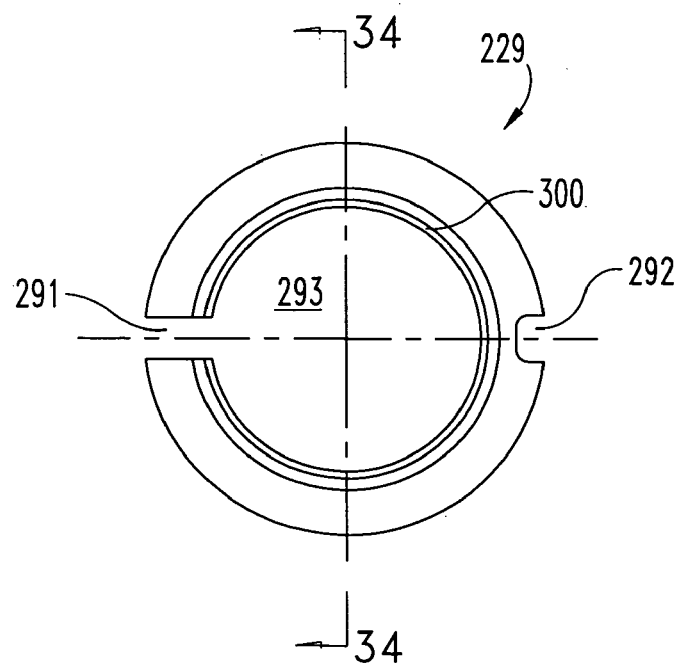
FIG. 33 is a side elevational view of the embodiment shown in FIG. 31, rotated 90 degrees from the view shown in FIG. 31.
Figure 34:
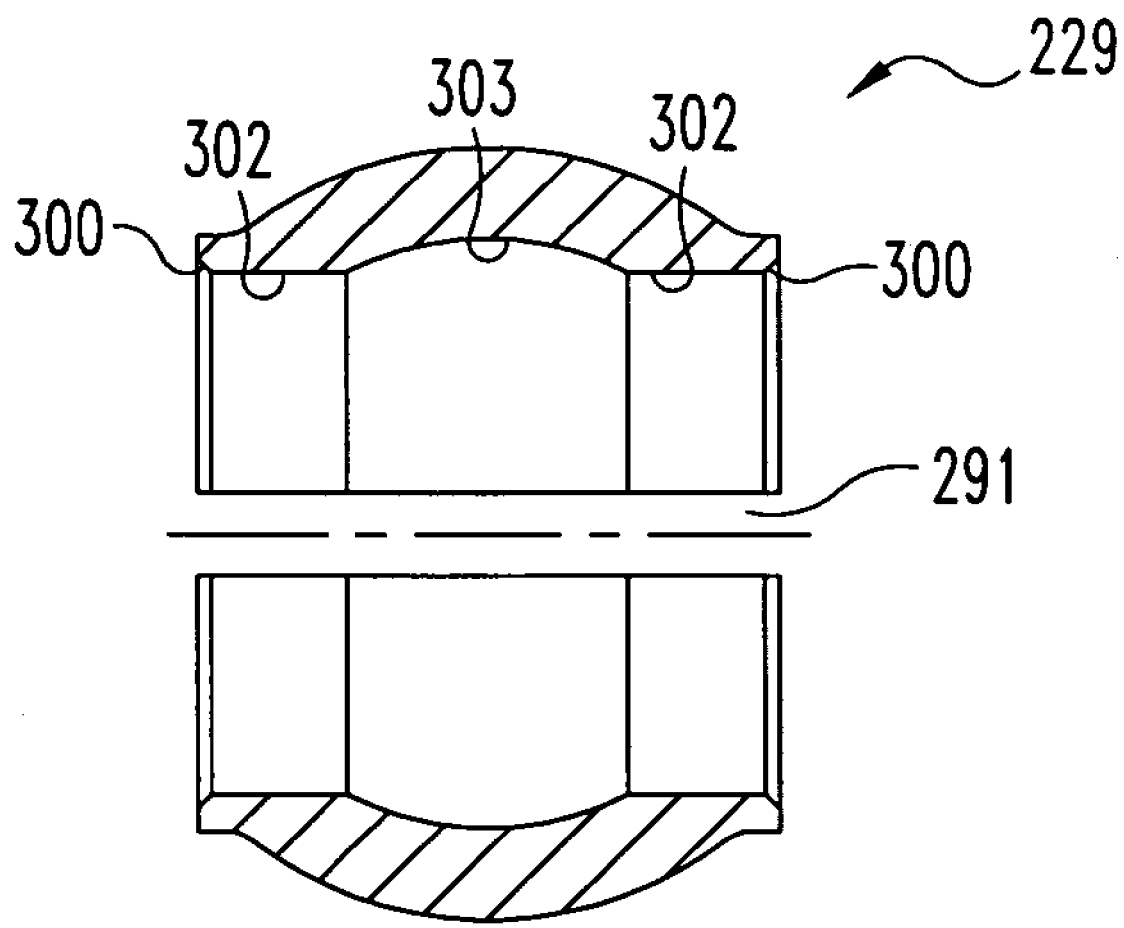
FIG. 34 is a cross-sectional view of the embodiment shown in FIG. 33, taken along the lines 34-34 in FIG. 33 and viewed in the direction of the arrows.
Figure 35:
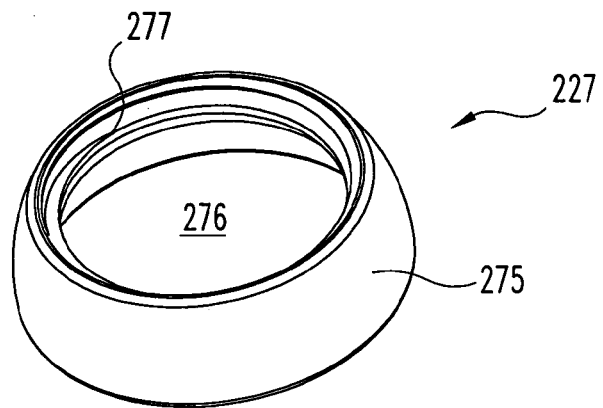
FIG. 35 is a perspective view of an embodiment of a washer member shown in FIG. 26.
Figure 36:
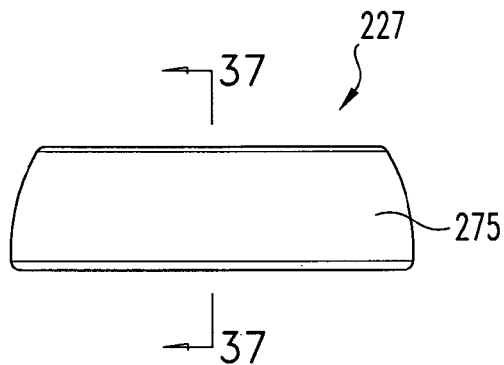
FIG. 36 is a side elevational view of the embodiment of a washer member shown in FIG. 35.
Figure 37:
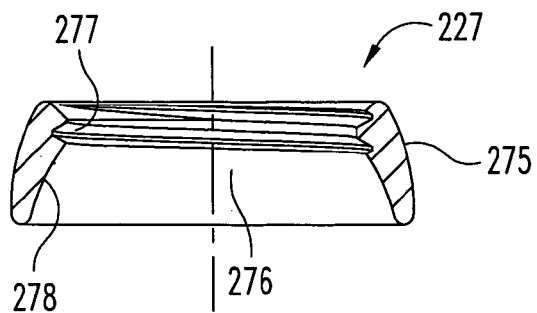
FIG. 37 is a cross-sectional view of the embodiment shown in FIG. 36, taken along the lines 37-37 in FIG. 36 and viewed in the direction of the arrows.
Figure 38:
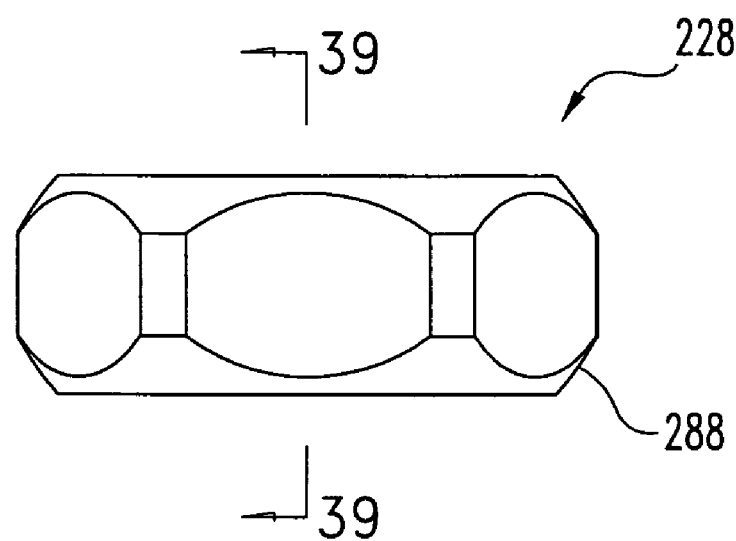
FIG. 38 is a side elevational view of an embodiment of a nut shown in FIG. 26.
Figure 39:
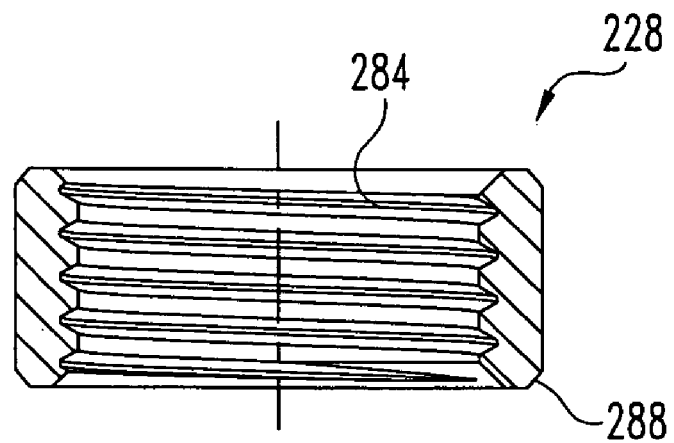
FIG. 39 is a cross-sectional view of the embodiment shown in FIG. 38, taken along the lines 39-39 in FIG. 38 and viewed in the direction of the arrows.
Figure 40:
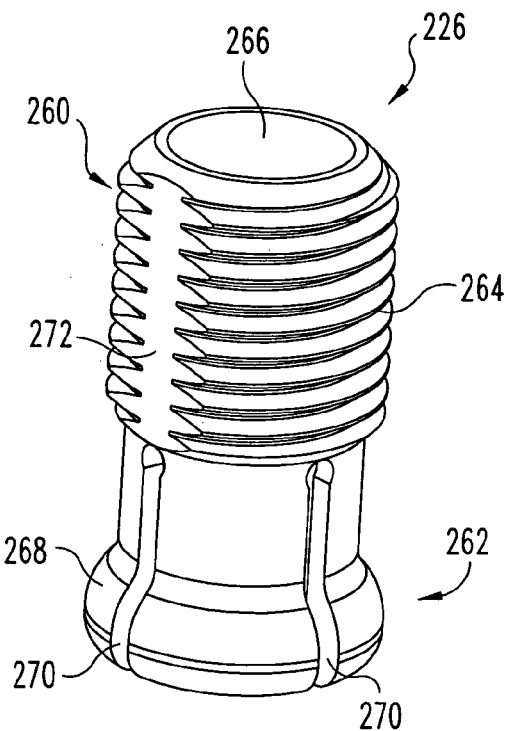
FIG. 40 is a perspective view of an embodiment of a collet member shown in FIG. 26.
Figure 41:
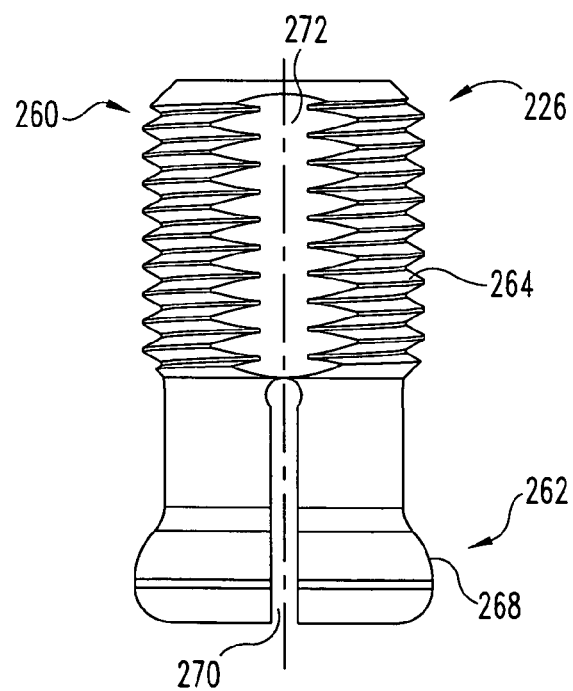
FIG. 41 is a side elevational view of the embodiment of a collet member shown in FIG. 40.

The illustrated embodiment of body 222 has an upper portion or surface 232 and a lower portion or surface 234. Upper surface 232 includes a slot 236 that may be substantially perpendicular to surface 232. Two passages 238 and 240 extend through body 222, and may be substantially parallel to each other. In a particular embodiment, passage 238 is substantially cylindrical throughout and is between surfaces 232 and 234, and passage 240 is substantially U-shaped. In other embodiments, passage 238 may be configured as discussed above with respect to passages 38 and 40. Passages 238 and 240 may be sized and configured to accommodate rods of similar or identical diameter or width, or as seen in FIG. 27, one passage may be somewhat larger than the other. Body 222 further defines a hole 242 extending therethrough and configured for receipt of an anchor (e.g. anchor 23 of FIG. 1) and collet 226, as will be discussed further below. Hole 242 may be substantially perpendicular to passages 238 and 240. A tapered or concave mouth 247, which may be substantially conical or otherwise configured, may be formed on upper surface 232 to extend around at least a portion of hole 242. A concavely curved portion 246 is adjacent bottom surface 234. As alternatives, hole 242 may include a lip or ridge (as described above) adjacent top surface 232, and portion 246 may be tapered, cylindrical, or otherwise curved.

Passage 238 may have internal surfaces of one or more configurations that allow placement of split ring member 229 and/or rods or other elongated members associated with them. For example, in the illustrated embodiment passage 238 includes a substantially cylindrical opening 238a on each side sized to facilitate placement of a ring member in passage 238. Inside tapered opening 238a is a grooved section 238b. Grooved section 238b, in the illustrated embodiment, is stepped, having a pair of edges 238c on either side of section 238b. As previously noted, features of passage 38 discussed above may be used in place of or in addition to features of passage 238, and vice versa. Passage 238 is compressible, as will be discussed further below.

Passage 240 in the illustrated embodiment is substantially U-shaped, and is internally threaded at or near the top. Threads 248 may be standard machine threads, or may be reverse-angle threads such as those disclosed in U.S. Pat. No. 6,296,642, incorporated herein by reference in its entirety. A set screw 250 (FIG. 27) is provided, which is configured to be threaded with threads 248 into passage 240.

The illustrated embodiment of collet 226 includes a proximal end 260 and a distal end 262. A threaded portion 264 extends along at least a portion of proximal end 260. An aperture 266 extends through collet 226. Collet 226 further includes a convex section 268 adjacent distal end 262, the function of which will be explained in greater detail below. Additionally, collet 226 includes one or more slots 270. In one embodiment, there are four slots 270 equally positioned about a circumference of collet 226 and which are generally parallel to aperture 266. Collet 226 includes one or more flat sections 272 adjacent proximal end 60 and threaded portion 64. In one embodiment, collet 226 includes two flat sections 272 positioned substantially diametrically opposite each other along the outside of collet 226 and along substantially the entire length of collet 226. Collet 226 is generally cylindrically shaped, except for flat sections 272 (if any). The outer cross-sectional dimension of collet 226 at convex section 268 is larger than an outer cross-sectional dimension of collet 226 at other points in the illustrated embodiment. Proximal portion of collet 226 is sized and shaped so as to fit and move easily within hole 242. However, collet 226 can be configured or shaped differently in other embodiments.

The illustrated embodiment of washer 227 is substantially annular, having a convex exterior 275 and a hole 276, which has a threaded portion 277 and a concave portion 278. Threaded interior portion 277 is configured to threadedly couple with threaded portion 264 of collet 226 to enable positioning of washer 247 about a portion of collet 226. At least a portion of the inner diameter of hole 276 is at least slightly smaller than an outer dimension of convex section 268 of collet 226. Exterior 275 and portion 278 may alternatively be conical or otherwise configured.

Nut 228, in one embodiment, is six-sided with a threaded hole 284 and a tapered or curved lower portion 288. Nut 228 is configured to be threaded on threaded portion 264 of collet 226. In other embodiments, nut 228 can be of other shapes or configurations, such as those discussed above. In another embodiment, nut 228' (FIG. 42) is similar to nut 28, and includes a lower substantially conical surface 288', the diameter of which decreases with distance from upper portion 280.

The illustrated embodiment of ring member 229 is generally annular, having a gap 291, notch 292 and through-hole 293 to allow expansion and/or contraction of ring member 29. The outside of ring member 229 has generally convex portions 294, which in a particular embodiment may be spherical. Extensions 298 extend outward from convex portions 294 and substantially surround hole 293. The inside of ring member 229 is for accommodating a rod, pin or other elongated orthopedic member, and in the illustrated embodiment includes tapered outer surfaces 300, substantially cylindrical inner surface 302 and curved (e.g. part-spherical) surface 303. Ring member 229 has an unstressed or natural outer diameter, i.e. a diameter measured when ring member 229 is under no contractive (gap-closing) or expansive (gap-opening) stress. Ring member 229 has an inner dimension measured diametrically between points on cylindrical portion 302 that, in one embodiment, is at least slightly larger than a diameter or similar dimension of a rod, pin or other elongated member.

The assembly, operation and use of assembly 220 is substantially similar to that described above with respect to assembly 20, and will now be described with reference to a surgical procedure involving a section of spine. Ring member 229 is inserted into passage 238 of body 222. In embodiments in which ring members 229 has an unstressed outer diameter larger than the inner dimension of passage 238, ring member 229 may be compressed to fit in passage 238, and released so that ring member 229 sits within passage 238. Washer 227 is threaded through threaded section 264 of collet 226 so that washer 227 sits atop convex section 268. Collet 226 and washer 227 are inserted into hole 242 of body 222 so that at least part of threaded portion 264 extends above body 222, and convex portion 275 of washer 227 is adjacent curved portion 246 of body 222. Nut 228 may be loosely threaded onto collet 226. These assembly steps may be performed in any of a variety of orders. For example, collet 226 and washer 227 may be inserted before ring member 229 is inserted into body 222. As another example, ring member 229 may be fitted onto an elongated member as described below, and then the elongated member and ring member can be inserted into passage 238. As yet a further example, collet 226 may first be placed over a positioned bone anchor as described below, and then washer 227 threaded onto collet 226, and the combination of collet 226, washer 227 and the bone anchor may be inserted into hole 242 of body 222.

A bone anchor (e.g. anchor 23 in FIG. 1), such as a Schanz-type screw, hook or other apparatus having a shank portion, is inserted into or otherwise connected to a bone, such as a vertebra (not shown). Assuming body 222, collet 226, washer 227, nut 228 and ring member 229 have been already assembled together as described above, assembly 220 is moved to a position adjacent the anchor and collet 226 is slid over the shank of the anchor. Assembly 220 is positioned along the anchor as the surgeon desires, and thus assembly 220 can be located at any height over the bone within a range determined by the length of the anchor exposed over the bone.

An elongated member may inserted through ring member 229, and another may be inserted into passage 240. In some embodiments, elongated members may be inserted in one or both of ring member 229 and passage 240 prior to placing assembly 220 over a bone anchor, and in other embodiments one or both elongated members may be inserted into assembly 220 after it is placed over such an anchor. In one particular method embodiment, an elongated member can be inserted through ring member 229 in body 222 and locked tightly or loosely, as described below, so as to hold body 222 with respect to the bone anchor, and then an elongated member can be placed in passage 240 and locked to provide additional support or further corrective force. Once placed within ring member 229 and assembly 220, an elongated member can be pivoted with respect to body 222 to any of a variety of angles. In doing so, ring member 229 is able to be rotated within passage 238. The pivoting of ring member 229 and/or its elongated member may be limited by contact of extension(s) 298 (if present on the ring member) with a surface of body 222 adjacent passage 238. If ring member 229 has a through-hole 293 of substantially different size than the width of passage 240, and elongated members of differing diameter or width are used, then generally the smaller elongated member should be placed through the smaller of through-hole 293 of ring member 229 and passage 240, and the larger elongated member should be placed through the larger of them.

When elongated members are positioned with respect to body 222 as the surgeon desires, and assembly 220 is at the desired position with respect to a bone anchor (e.g. bone anchor 23 in FIG. 1), the surgeon may tighten nut 228. In this embodiment, tightening nut 228 around collet 226 draws collet 226 in hole 242 so that convex section 268 squeezes washer 227 against surface 246 of body 222, with the reaction that convex section 268 contracts around the anchor by virtue of slots 270. Such contraction of collet 226 around the anchor locks the anchor with respect to collet 226 and body 222 at the desired relative position. At the same time, nut 228 exerts a pushing force on upper surface 232 of body 222. Such pushing forces down the side of upper surface 232 adjacent passage 238, essentially pivoting that side of upper surface 32 around an axis in or near the side of body 222 adjacent passage 238, and compresses passage 238. Compressing passage 238 results in similar compression of ring member 229, locking ring member 229 around its elongated member. Ring member 229 may be penetrated or otherwise interacted with by edges 238c in passage 238 during such compression. Thus, tightening nut 228 locks assembly 220 with respect to both the bone anchor and an elongated member in passage 238. An elongated member placed in passage 240 is locked with respect to body 222 by threading a set screw 250 into threads 248 in passage 240 and against the elongated member.

Standard surgical approaches, whether open or minimally-invasive, may be used in connection with the steps noted above. For example, the surgeon may obtain access to the surgical site in a manner well known in the art, e.g. through incision and retraction of tissues. Once access to the surgical site has been obtained, e.g. via an opening such as a midline incision above the affected area, with tissue being resected laterally or in other appropriate direction, or by other surgical procedure, pilot holes in bones may be made (e.g. in a pedicle of a vertebra), and screws may be inserted into such holes.

It will be seen that split ring members (e.g. 29, 30, 229 or 230) may not be necessary in some embodiments. For example, in embodiments in which the diameter of an elongated member is not a great deal smaller than the diameter of passages 38, 40, 238 and/or 240 or in a case in which the pivotability of ring members with respect to a connector body is not needed or desired, one or more elongated members can be placed through connector passages (e.g. passages 38, 40, 238 and/or 240). The passages are compressed, as discussed above, and lock directly to the elongated members.

Although useful with two elongated members, the disclosed embodiments of body 22, 222 may be used with only one elongated member, if desired. Further, multiple elongated members (e.g. thin pins) could be connected to a connector body substantially as described above. Elongated members may be substantially cylindrical or of other cross-sectional shapes, and may be smooth, threaded, knurled or otherwise surfaced.

In certain embodiments, a collet member as described above may be omitted where a bone anchor has a shank with a threaded portion and an enlarged medial portion that can contact the bottom of a connector body (e.g. body 22 or 222).

The parts described above may be interchanged among the described embodiments or other embodiments. For example, collet member 226 may be used with body 22. In other embodiments, nuts 28, 228 could be replaced with another tightening mechanism. The various components described above may be composed of biocompatible materials such as titanium, stainless steel, certain ceramics or plastics, or others.

While subject matter has been illustrated and described in detail in the drawings and foregoing description, the same is to be considered as illustrative and not restrictive in character. It should be understood that only certain embodiments have been shown and described and that all changes and modifications that come within the spirit of the claims are desired to be protected.

What is claimed is:

1. An apparatus comprising:
   a connector body having two passages for elongated members and an anchor passage between said elongated member passages, each of said passages having a respective diameter,
   said body having a top portion and a bottom portion, said anchor passage extending through said portions from an upper surface of said top portion to a lower surface of said bottom portion, and said top portion having a slot running substantially parallel with said anchor passage that communicates with said anchor passage,
   said top portion being bendable so that bending at least part of said top portion toward said bottom portion reduces the diameter of at least one of said elongated member passages, and
   wherein said top portion has a first side part generally over a first of said passages and a second side part generally over a second of said passages, said first and second side parts being separated by said slot, and wherein said first side part is bendable around a first axis adjacent said first passage, and said second side part is bendable around a second axis adjacent said second passage; and
   wherein bending said first and second side parts of said top portion reduces the diameter of both of said first and second passages; and
   wherein said connector body includes opposite side portions that each extend continuously between said top and bottom portions to enclose said first and second passages.

2. The apparatus of claim 1, further comprising at least one split ring member inserted at least partially into one of said elongated member passages, said split ring member having a hole therethrough sized to accommodate an elongated member, and said split ring member being compressible around the elongated member.

3. The apparatus of claim 2, further comprising at least one tab positioned between a first end and a second end of said at least one split ring member and extending from an outer surface of said split ring member for limiting rotation of said split ring member relative to said body.

4. The apparatus of claim 1, further comprising an anchor extending through said anchor passage.

5. The apparatus of claim 4, wherein said anchor includes a shaft, and further comprising a collet having a threaded upper portion, a slotted lower portion, and a longitudinal aperture, said shaft extending at least part way through said aperture.

6. The apparatus of claim 4, further comprising a nut connectable with said anchor and said body, wherein tightening said nut on said anchor forces said nut against said first and second side parts of said top portion defined by said slot and movable relative to one another, thereby bending said first and second side parts of said top portion toward said bottom portion of said body.

7. The apparatus of claim 1, wherein said body is a single piece.

8. The apparatus of claim 1, further comprising an anchor positioned within said anchor passage; and
wherein said anchor exerts a pushing force onto each of said first and second side parts of said top portion at said slot to simultaneously bend said first and second side parts toward said bottom portion of said body and reduce the diameter of each of said first and second passages.

9. The apparatus of claim 1, wherein said first axis comprises a first pivot axis positioned in a first of said opposite side portions of said connector body directly adjacent said first passage, said first side portion pivots about said first pivot axis to reduce the diameter of said first passage and capture a first of said elongated members within said first passage; and
wherein said second axis comprises a second pivot axis positioned in a second of said opposite side portions of said connector body directly adjacent said second passage, said second side portion pivots about said second pivot axis to reduce the diameter of said second passage and capture a second of said elongated members within said second passage.

10. An apparatus comprising:
an orthopedic implant having a bottom portion for facing bone and a bifurcated top portion, wherein said bifurcated top portion defines a first slot on a front surface and a second slot on a rear surface and including a first lateral portion extending from said first and second slots to a first lateral side of said top portion, said first lateral portion being separated from a second lateral portion extending from said first and second slots to a second lateral side of said top portion, each of said first and second lateral portions being movable relative to the other of said first and second lateral portions and bendable toward said bottom portion, and said implant including a first passage between said bottom portion and said top portion and a second passage between said bottom portion and said top portion, wherein when said top portion is bent toward said bottom portion said first lateral portion is bendable around a first axis located adjacent said first passage and said second lateral portion is bendable around a second axis located adjacent said second passage to thereby reduce the size of each of said first and second passages, wherein said implant includes opposite side portions that each extend continuously between said top and bottom portions to enclose said first and second passages.

11. The apparatus of claim 10, further comprising a first elongated member at least partially within said first passage, and a second elongated member at least partially within said second passage.

12. The apparatus of claim 11, further comprising a split ring member in said first passage and between said first elongated member and said implant, so that when the size of said first passage is reduced, said split ring member is compressed around said first elongated member.

13. An apparatus comprising:
a connector body having first and second substantially parallel passages, and a third passage substantially perpendicular to said first and second passages, and further having a top surface, a bottom surface and two side surfaces, said top surface having a slot therethrough, said slot running through said top surface substantially parallel to said third passage and aligned and in communication with said third passage at said top surface, wherein each said side surfaces of said connector body extend continuously between said top and bottom surfaces to enclose said first and second passages;
a first split ring member at least partially in said first passage and a second split ring member at least partially in said second passage, said split ring members each having a through hole for accommodating at east part of an elongated member and a curved external surface whereby said split ring member can be pivoted with respect to said body;
a pair of elongated members, one of said elongated members occupying at least part of said through hole of said first split ring member and the other of said elongated members occupying at least part of said through hole of said second split ring member;
a bone anchor extending through said third passage, said bone anchor having an upper threaded portion; and
a nut threaded onto said threaded portion of said bone anchor and against said top surface of said connector body, wherein tightening said nut against said top surface bends a first lateral portion of said top surface around a first axis located adjacent said first passage and bends a second lateral portion of said top surface around a second axis located adjacent said second passage so that said first and second passages are reduced in size and so that said split ring members are compressed around said elongated members to lock said elongated members with respect to said connector body.

14. The apparatus of claim 13, wherein said through hole of said first split ring member has a diameter less than that of said second split ring member.

15. The apparatus of claim 13, wherein said bottom surface includes a concavely curved portion against which a portion of said anchor may bear.

16. The apparatus of claim 13, wherein at least one of said passages has a conical opening portion and a substantially cylindrical internal portion.

17. The apparatus of claim 13, wherein at least one of said passages has a stepped internal portion having at least one edge.

18. The apparatus of claim 13, wherein said top surface includes a conical indentation, and said nut includes a conical underside configured to substantially mate with said conical indentation.

19. An apparatus comprising:
a connector body having a first passage for a first elongated member, a second passage for a second elongated member and an anchor passage between said first and second passages;
said connector body having a top portion and a bottom portion, said anchor passage extending through said portions from an upper surface of said top portion to a lower surface of said bottom portion, and said top portion having a slot running substantially parallel with said anchor passage that communicates with said anchor passage;

an anchor positioned within said anchor passage, said top portion being bendable so that bending at least part of said top portion toward said bottom portion reduces the diameter of said first passage, said anchor exerts a pushing force onto said at least part of said top portion at said slot and pivots said top portion about a pivot axis located in a side of said connector body directly adjacent said first passage to bend said top portion toward said bottom portion and reduce the diameter of said first passage and capture said first elongated member positioned within said first passage; and wherein said second passage is substantially U-shaped and is at least partially internally threaded, and further comprising a set screw configured to thread into said U-shaped passage and capture said second elongated member positioned within said second passage.

20. An apparatus comprising:

an orthopedic implant having a bottom portion for facing bone and a bifurcated top portion, wherein said bifurcated top portion defines a first slot on a front surface and a second slot on a rear surface and including a first lateral portion extending from said first and second slots to a first lateral side of said top portion, said first lateral portion being separated from a second lateral portion extending from said first and second slots to a second lateral side of said top portion, each of said first and second lateral portions being movable relative to the other of said first and second lateral portions and bendable toward said bottom portion, and said implant including a first passage between said bottom portion and said top portion and a second passage between said bottom portion and said top portion, wherein when said top portion is bent toward said bottom portion said first lateral portion is bendable around a first axis located adjacent said first passage and said second lateral portion is bendable around a second axis located adjacent said second passage to thereby reduce the size of each of said first and second passages, further comprising an anchor passage between said first and second passages and extending through said top and bottom portions and communicating with said first and second slots; and an anchor positioned within said anchor passage; and wherein said anchor exerts a pushing force onto each of said first and second lateral portion at said first and second slots to simultaneously bend said first and second lateral portions toward said bottom portion and reduce the size of each of said first and second passages.

21. An apparatus comprising:

an orthopedic implant having a bottom portion for facing bone and a bifurcated top portion, wherein said bifurcated top portion defines a first slot on a front surface and a second slot on a rear surface and including a first lateral portion extending from said first and second slots to a first lateral side of said top portion, said first lateral portion being separated from a second lateral portion extending from said first and second slots to a second lateral side of said top portion, each of said first and second lateral portions being movable relative to the other of said first and second lateral portions and bendable toward said bottom portion, and said implant including a first passage between said bottom portion and said top portion and a second passage between said bottom portion and said top portion, wherein when said top portion is bent toward said bottom portion said first lateral portion is bendable around a first axis located adjacent said first passage and said second lateral portion is bendable around a second axis located adjacent said second passage to thereby reduce the size of each of said first and second passages, wherein said first axis comprises a first pivot axis positioned in a first side of said implant directly adjacent said first passage, said first lateral portion pivots about said first pivot axis to reduce the size of said first passage and capture a first elongated member within said first passage; and wherein said second axis comprises a second pivot axis positioned in a second side of said implant directly adjacent said second passage, said second lateral portion pivots about said second pivot axis to reduce the size of said second passage and capture a second elongated member within said second passage.

22. The apparatus of claim 21, wherein said implant includes opposite side portions that each extend continuously between said top and bottom portions to enclose said first and second passages.

23. An apparatus comprising:

a connector body having first and second substantially parallel passages, and a third passage substantially perpendicular to said first and second passages, and further having a top surface, a bottom surface and two side surfaces, said top surface having a slot therethrough, said slot running through said top surface substantially parallel to said third passage and aligned and in communication with said third passage at said top surface;

a first split ring member at least partially in said first passage and a second split ring member at least partially in said second passage, said split ring members each having a through hole for accommodating at least part of an elongated member and a curved external surface whereby said split ring member can be pivoted with respect to said body;

a pair of elongated members, one of said elongated members occupying at least part of said through hole of said first split ring member and the other of said elongated members occupying at least part of said through hole of said second split ring member;

a bone anchor extending through said third passage, said bone anchor having an upper threaded portion; and a nut threaded onto said threaded portion of said bone anchor and against said top surface of said connector body, wherein tightening said out against said top surface bends a first lateral portion of said top surface around a first axis located adjacent said first passage and bends a second lateral portion of said top surface around a second axis located adjacent said second passage so that said first and second passages are reduced in size and so that said split ring members are compressed around said elongated members to lock said elongated members with respect to said connector body; and wherein said bone anchor and said nut cooperate to exert a pushing force onto each of said first and second lateral portions at said slot to simultaneously bend said first and second lateral portions toward said bottom surface and reduce the size of each of said first and second passages.

24. An apparatus comprising:

a connector body having first and second substantially parallel passages, and a third passage substantially perpendicular to said first and second passages, and further having a top surface, a bottom surface and two side surfaces, said top surface having a slot therethrough, said slot running through said top surface substantially parallel to said third passage and aligned and in communication with said third passage at said top surface;

a first split ring member at least partially in said first passage and a second split ring member at least partially in said second passage, said split ring members each having a through hole for accommodating at least part of an elongated member and a curved external surface whereby said split ring member can be pivoted with respect to said body;

a pair of elongated members, one of said elongated members occupying at least part of said through hole of said first split ring member and the other of said elongated members occupying at least part of said through hole of said second split ring member;

a bone anchor extending through said third passage, said bone anchor having an upper threaded portion; and a nut threaded onto said threaded portion of said bone anchor and against said top surface of said connector body, wherein tightening said nut against said top surface bends a first lateral portion of said top surface around a first axis located adjacent said first passage and bends a second lateral portion of said top surface around a second axis located adjacent said second passage so that said first and second passages are reduced in size and so that said split ring members are compressed around said elongated members to lock said elongated members with respect to said connector body; and wherein said first axis comprises a first pivot axis positioned in a first side of said connector body directly adjacent said first passage, said first lateral portion pivots about said first pivot axis to reduce the size of said first passage and capture a first of said elongated members within said first passage; and wherein said second axis comprises a second pivot axis positioned in a second side of said connector body directly adjacent said second passage, said second lateral portion pivots about said second pivot axis to reduce the size of said second passage and capture a second of said elongated members within said second passage.

25. The apparatus of claim 24, wherein each said side surfaces of said connector body extend continuously between said top and bottom surfaces to enclose said first and second passages.

* * * * *

UNITED STATES PATENT AND TRADEMARK OFFICE
CERTIFICATE OF CORRECTION

| | | |
|---|---|---|
| PATENT NO. | : 7,803,174 B2 | Page 1 of 1 |
| APPLICATION NO. | : 11/266991 | |
| DATED | : September 28, 2010 | |
| INVENTOR(S) | : Denis et al. | |

It is certified that error appears in the above-identified patent and that said Letters Patent is hereby corrected as shown below:

In Column 12, Line 18, in Claim 13, delete "east" and insert -- least --, therefor.

In Column 14, Line 43, in Claim 23, delete "out" and insert -- nut --, therefor.

Signed and Sealed this
Twenty-sixth Day of April, 2011

David J. Kappos
*Director of the United States Patent and Trademark Office*